United States Patent
Elomari et al.

(10) Patent No.: US 8,115,040 B2
(45) Date of Patent: Feb. 14, 2012

(54) COMPOSITION OF A SUPERIOR LUBRICANT OR LUBRICANT BLENDSTOCK

(75) Inventors: Saleh Elomari, Fairfield, CA (US); Russell R. Krug, Novato, CA (US)

(73) Assignee: Chevron U.S.A. Inc., Sam Ramon, CA (US)

( * ) Notice: Subject to any disclaimer, the term of this patent is extended or adjusted under 35 U.S.C. 154(b) by 631 days.

(21) Appl. No.: 12/261,388

(22) Filed: Oct. 30, 2008

(65) Prior Publication Data

US 2009/0050521 A1     Feb. 26, 2009

Related U.S. Application Data

(62) Division of application No. 11/316,155, filed on Dec. 20, 2005, now Pat. No. 7,572,944.

(51) Int. Cl.
*C10M 171/02* (2006.01)
*C10M 171/04* (2006.01)
(52) U.S. Cl. ........................................ 585/332; 508/110
(58) Field of Classification Search ................... 585/332; 508/110
See application file for complete search history.

(56) References Cited

U.S. PATENT DOCUMENTS

| | | | |
|---|---|---|---|
| 5,750,455 A | 5/1998 | Chauvin et al. | |
| 6,028,024 A | 2/2000 | Hirschauer et al. | |
| 6,395,948 B1 | 5/2002 | Hope et al. | |
| 7,045,055 B2 * | 5/2006 | Ziemer et al. | 208/18 |
| 2001/0001804 A1 | 5/2001 | Skledar et al. | |
| 2004/0267071 A1 * | 12/2004 | Harris et al. | 585/329 |

FOREIGN PATENT DOCUMENTS

EP     0791643     8/1997

OTHER PUBLICATIONS

PCT/US06/46907, Written Opinion of the International Searching Authority, 3 pages, mailed date Sep. 13, 2007.
Australian Government IP Australia letter, 2 pages, mailed date Jun. 20, 2011.

* cited by examiner

*Primary Examiner* — Jim Goloboy
(74) *Attorney, Agent, or Firm* — Susan M. Abernathy; David Tuck

(57) ABSTRACT

A composition of a superior lubricant or lubricant component having a very high VI, a low cloud point, a difference between the T90 and T10 boiling points of at least 250° F. by SIM-DIST, and a very low Bromine Number.

20 Claims, No Drawings

COMPOSITION OF A SUPERIOR LUBRICANT OR LUBRICANT BLENDSTOCK

This application is a divisional of U.S. patent application Ser. No. 11/316,155, filed Dec. 20, 2005, and herein incorporated in its entirety.

BACKGROUND OF THE INVENTION

Olefin oligomers and relatively long chain olefins can be used in the production of high value lubricant components or blendstocks. One problem with the use of olefin oligomers in either of the above uses is that the olefinic double bond can be undesirable. Olefinic double bonds cause problems in both fuels and in lubricants. Olefin oligomers can further oligomerize forming 'gum' deposits in the fuel. Olefins in fuel are also associated with air quality problems. Olefins can also oxidize which can be a particular problem in lubricants. One way of minimizing the problem is to hydrogenate some or all of the double bonds to form saturated hydrocarbons. A method of doing this is described in US published Application US 2001/0001804 which is incorporated herein in its entirety. Hydrogenation can be an effective way to minimize the concentration of olefins in the lubricant or fuel however it requires the presence of hydrogen and a hydrogenation catalyst both of which can be expensive. Also excessive hydrogenation can lead to hydrocracking. Hydrocracking can increase as one attempts to hydrogenate the olefins to increasingly lower concentrations. Hydrocracking is generally undesirable as it produces a lower molecular weight material where the goal in oligomerization is to produce a higher molecular weight material. Directionally it would generally be preferred to increase, not decrease the average molecular weight of the material. Thus using the hydrogenation method it is desired to hydrogenate the olefins as thoroughly as possible while minimizing any hydrocracking or hydrodealkylation. This is inherently difficult and tends to be a compromise.

Hydrocracking of a slightly branched hydrocarbon material can also lead to less branching. Cracking tends to be favored at the tertiary and secondary centers. For example a branched hydrocarbon can crack at a secondary center forming two more linear molecules which is also directionally undesirable.

Potentially, Ionic Liquid catalyst systems can be used for the oligomerization of olefins such as normal alpha olefins to make olefin oligomers. A Patent that describes the use of an ionic liquid catalyst to make polyalphaolefins is U.S. Pat. No. 6,395,948 which is incorporated herein by reference in its entirety. A published application that discloses a process for oligomerization of alpha olefins in ionic liquids is EP 791,643.

Ionic Liquid catalyst systems have also been used for isoparaffin-olefin alkylation reactions. Patents that disclose a process for the alkylation of isoparaffins by olefins are U.S. Pat. No. 5,750,455 and U.S. Pat. No. 6,028,024.

It would be desirable to have a process for making a lubricant or lubricant starting materials with low degree of unsaturation (low concentration of double bonds) thus reducing the need for exhaustive hydrogenation while preferably maintaining or more preferably increasing the average molecular weight and branching of the material while also increasing the lubricant properties of the product. The present invention provides a new composition with just such desired features.

SUMMARY OF THE INVENTION

We provide a lubricant component or base oil, comprising: a cloud point of less than −50° C.; a Viscosity Index (VI) of at least 134; a difference between the T90 and T10 boiling points of at least 250° F. by Simulated Distillation (SIMDIST); and a Bromine Number of less than 0.2

DETAILED DESCRIPTION OF THE INVENTION

The present invention provides a novel process for the production of lubricant or lubricant components by the acid catalyzed oligomerization of olefins and alkylation with isoparaffins in ionic liquid medium to form a product having greatly reduced olefin content and improved quality. Amazingly, we found that oligomerization of an olefin and alkylation of an olefin and/or its oligomers with an isoparaffin can be performed together in a single reaction zone or alternatively in two separate zones. The alkylated or partially alkylated oligomer stream that results has very desirable properties for use as a lubricant or lubricant blendstock. In particular the present invention provides a process for making a lubricant, base oil, lubricant component, or solvent having improved properties such as increased branched, higher molecular weight, and low Bromine Number. The present invention also provides a composition of a lubricant component or base oil having improved properties including a cloud point of less than −50 or −55° C.; a VI of at least 134 or 140; a difference between the T90 and T10 boiling points of at least 250 or 300° F. by SIMDIST; and a Bromine Number of less than 0.2.

Oligomerization of two or more olefin molecules results in the formation of an olefin oligomer that generally comprises a long branched chain molecule with one remaining double bond. The present invention provides a novel way to reduce the concentration of double bonds and at the same time enhance the quality of the desired fuel or lubricant. This invention also reduces the amount of hydrofinishing that is needed to achieve a desired product with low olefin concentration. The olefin concentration can be determined by Bromine Index or Bromine Number. Bromine Number can be determined by test ASTM D 1159. Bromine Index can be determined by ASTM D 2710. Test methods D 1159 and ASTM D 2710 are incorporated herein by reference in their entirety. Bromine Index is effectively the number of milligrams of Bromine ($Br_2$) that react with 100 grams of sample under the conditions of the test. Bromine Number is effectively the number of grams of bromine that will react with 100 grams of specimen under the conditions of the test.

In a preferred embodiment of the present invention, HCl or a component that directly or indirectly supplies protons is added to the reaction mixture. Although not wishing to be limited by theory it is believed that the presence of a Brönsted acid such as HCl greatly enhances the acidity and, thus, the activity of the ionic liquid catalyst system.

Among other factors, the present invention involves a surprising new way of making a lubricant base oil or lubricant blendstock that has reduced levels of olefins without hydrogenation or with minimal hydrofinishing. The present invention also increases the value of the resultant olefin oligomers by increasing the molecular weight of the oligomer and increasing the branching by incorporation of isoparaffin groups into the oligomers' skeletons. These properties can both add significant value to the product particularly when starting with a highly linear hydrocarbon such as the preferred feeds to the present invention (i.e. Fischer-Tropsch derived hydrocarbons). The product of the present invention can have a combination of highly desirable and novel qualities for a lubricant component or base oil including a very high VI with a very low cloud point while having a fairly wide boiling range. The present invention is based on the use of an ionic liquid catalyst to alkylate an oligomerized olefin with an isoparaffin under relatively mild conditions. The alkylation optionally can occur under effectively the same conditions as oligomerization. This finding that alkylation and oligomerization reactions can occur using effectively the same ionic liquid catalyst system and optionally under similar or even the same conditions can be used to make a highly integrated, synergistic process resulting in an alkylated oligomer product having desirable properties. Also in a particular embodiment of the present invention the alkylation and oligomerization reactions can occur simultaneously under the same conditions.

A preferred catalyst system of the present invention is an acidic chloroaluminate ionic liquid system. More preferably the acidic chloroaluminate ionic liquid system is used in the presence of a Brönsted acid. Preferably the Brönsted acid is a halohalide and most preferably is HCl.

The oligomerization reaction and the alkylation reaction in the present invention can be performed together or separately. An advantage of combining the oligomerization and alkylation is lower capital and operating costs. An advantage of the 2 step process (oligomerization followed by alkylation in a separate zone) is that the two separate reaction zones can be optimized independently. Thus the conditions for oligomerization zones can be different than the alkylation zone conditions. Also the ionic liquid catalyst can be different in the different zones. For instance, it may be preferable to make the alkylation zone more acidic than the oligomerization zone. This may involve the use of an entirely different ionic liquid catalyst in the two zones or can be by addition of a Brönsted acid to the alkylation zone.

In a preferred embodiment of the present invention, the ionic liquid used in alkylation zone and in the oligomerization zone is the same. This helps save on catalyst costs, potential contamination issues, and provides synergy opportunities in the process.

As discussed above, the present invention produces a product having a very low cloud point and a very high VI. Cloud Point can be determined by ASTM D 2500. VI can be determined by ASTM D 2270. ASTM test methods D 2500 and D D2270 are incorporated by reference herein in their entirety.

In the present application, distillation data was generated for several of the products by SIMDIST. SIMDIST involves the use of ASTM D 6352 or ASTM D 2887 as appropriate. ASTM D 6352 and ASTM D 2887 are incorporated herein by reference in their entirety. Distillation data can also be generated using ASTM D86 which is incorporated herein by reference in its entirety.

In the present application the terms lubricant base oil, lubricant blendstock, and lubricant component are used to mean lubricant components that can be used to produce a finished lubricant.

Ionic Liquids

Ionic liquids are a class of compounds made up entirely of ions and are generally liquids at ambient and near ambient temperatures. Often salts which are composed entirely of ions are solids with high melting points, for example, above 450° C. These solids are commonly known as 'molten salts' when heated to above their melting points. Sodium chloride, for example, is a common 'molten salt', with a melting point of 800° C. Ionic liquids differ from 'molten salts', in that they have low melting points, for example, from −100° C. to 200° C. Ionic liquids tend to be liquids over a very wide temperature range, with some having a liquid range of up to 300° C. or higher. Ionic liquids are generally non-volatile, with effectively no vapor pressure. Many are air and water stable, and can be good solvents for a wide variety of inorganic, organic, and polymeric materials.

The properties of ionic liquids can be tailored by varying the cation and anion pairing. Ionic liquids and some of their commercial applications are described, for example, in J. Chem. Tech. Biotechnol, 68:351-356 (1997); J. Phys. Condensed Matter, 5:(supp 34B):B99-B106 (1993); Chemical and Engineering News, Mar. 30, 1998, 32-37; J. Mater. Chem., *:2627-2636 (1998); and Chem. Rev., 99:2071-2084 (1999), the contents of which are hereby incorporated by reference.

Many ionic liquids are amine-based. Among the most common ionic liquids are those formed by reacting a nitrogen-containing heterocyclic ring (cyclic amines), preferably nitrogen-containing aromatic rings (aromatic amines), with an alkylating agent (for example, an alkyl halide) to form a quaternary ammonium salt, followed by ion exchange with Lewis acids or halide salts, or by anionic metathesis reactions with the appropriate anion sources to introduce the desired counter anionic to form ionic liquids. Examples of suitable heteroaromatic rings include pyridine and its derivatives, imidazole and its derivatives, and pyrrole and its derivatives. These rings can be alkylated with varying alkylating agents to incorporate a broad range of alkyl groups on the nitrogen including straight, branched or cyclic $C_{1-20}$ alkyl group, but preferably $C_{1-12}$ alkyl groups since alkyl groups larger than $C_{1-12}$ may produce undesirable solid products rather than ionic liquids. Pyridinium and imidazolium-based ionic liquids are perhaps the most commonly used ionic liquids. Other amine-based ionic liquids including cyclic and non-cyclic quaternary ammonium salts are frequently used. Phosphonium and sulphonium-based ionic liquids have also been used.

Counter anions which have been used include chloroaluminate, bromoaluminate, gallium chloride, tetrafluoroborate, tetrachloroborate, hexafluorophosphate, nitrate, trifluoromethane sulfonate, methylsulfonate, p-toluenesulfonate, hexafluoroantimonate, hexafluoroarsenate, tetrachloroaluminate, tetrabromoaluminate, perchlorate, hydroxide anion, copper dichloride anion, iron trichloride anion, antimony hexafluoride, copper dichloride anion, zinc trichloride anion, as well as various lanthanum, potassium, lithium, nickel, cobalt, manganese, and other metal ions. The ionic liquids used in the present invention are preferably acidic haloaluminates and preferably chloroaluminates.

The organic cations in the ionic liquid of the present invention can be selected from the group consisting of pyridinium-based and imidazolium-based cations. Cations that have been found to be particularly useful in the process of the present invention include pyridinium-based cations.

Preferred ionic liquids that can be used in the process of the present invention include acidic chloroaluminate ionic liquids. Preferred ionic liquids used in the present invention are acidic pyridinium chloroaluminates. More preferred ionic liquids useful in the process of the present invention are alkyl-pyridinium chloroaluminates. Still more preferred ionic liquids useful in the process of the present invention are alkyl-pyridinium chloroaluminates having a single linear alkyl group of 2 to 6 carbon atoms in length. One particular ionic liquid that has proven effective is 1-butyl-pyridinium chloroaluminate.

In a more preferred embodiment of the present invention 1-butyl-pyridinium chloroaluminate is used in the presence of a Brönsted acid. Not to be limited by theory, the Brönsted acid acts as a promoter or co-catalyst. Examples of Brönsted acids are Sulfuric, HCl, HBr, HF, Phosphoric, HI, etc. Other protic acids or species that directly or indirectly aid in supplying protons may also be used as Brönsted acids or in place of Brönsted acids.

The Feeds

In the process of the present invention one of the important feedstocks comprises a reactive olefinic hydrocarbon. The olefinic group provides the reactive site for the oligomerization reaction as well as the alkylation reaction. The olefinic hydrocarbon can be a fairly pure olefinic hydrocarbon cut or can be a mixture of hydrocarbons having different chain lengths thus a wide boiling range. The olefinic hydrocarbon can be terminal olefin (an alpha olefin) or can be internal olefin (internal double bond). The olefinic hydrocarbon chain can be either straight chain or branched or a mixture of both. The feedstocks useable in the present invention can include unreactive diluents such as normal paraffins.

In one embodiment of the present invention, the olefinic feed comprises a mixture of mostly linear olefins from $C_2$ to about $C_{30}$. The olefins are mostly but not entirely alpha olefins.

In another embodiment of the present invention, the olefinic feed can comprise at least 50% of a single alpha olefin species.

In another embodiment of the present invention, the olefinic feed can be comprised of an NAO cut from a high purity Normal Alpha Olefin (NAO) process made by ethylene oligomerization.

In an embodiment of the present invention, some or all of the olefinic feed to the process of the present invention comprises thermally cracked hydrocarbons, preferably cracked wax, and more preferably cracked wax from a Fischer-Tropsch (FT) process. A process for making olefins by cracking FT products is disclosed in U.S. Pat. No. 6,497,812 which is incorporated herein by reference in its entirety.

In the process of the present invention, another important feedstock is an isoparaffin. The simplest isoparaffin is isobutane. Isopentanes, isohexanes, isoheptanes, and other higher isoparaffins are also useable in the process of the present invention. Economics and availability are the main drivers of the isoparaffins selection. Lighter isoparaffins tend to be less expensive and more available due to their low gasoline blend value (due to their relatively high vapor pressure). Mixtures of light isoparaffins can also be used in the present invention. Mixtures such as $C_4$-$C_5$ isoparaffins can be used and may be advantaged because of reduced separation costs. The isoparaffins feed stream may also contain diluents such as normal paraffins. This can be a cost savings, by reducing the cost of separating isoparaffins from close boiling paraffins. Normal paraffins will tend to be unreactive diluents in the process of the present invention.

In an optional embodiment of the present invention the resultant alkylated oligomer made in the present invention can be hydrogenated to further decrease the concentration of olefins and thus the Bromine Number. After hydrogenation, the lubricant component or base oil has a Bromine Number of less than 0.8, preferably less than 0.5, more preferably less than 0.3, still more preferably less than 0.2.

Alkylation conditions for the process of the present invention include a temperature of from about 15 to about 200° C., preferably from about 20 to about 150° C., more preferably from about 25 to about 100, and most preferably from 50 to 100° C.

Oligomerization conditions for the process of the present invention include a temperature of from about 0 to about 150° C., from about 10 to about 100° C., or from about 0 to about 50.

As discussed elsewhere in the present application the oligomerization and the alkylation can occur separately (in separate optimized zones) or can occur together. In the embodiment where the alkylation and oligomerization occur together, optimum conditions for either reaction may have to be compromised. However, surprisingly the conditions can be adjusted to achieve both substantial oligomerization and alkylation and resulting in a valuable lubricant base oil or blendstock.

In summary, the potential benefits of the process and composition of the present invention include:
  Reduced capital cost for hydrotreating/hydrofinishing
  Lower operating cost due to reduced hydrogen and extensive hydrogenation requirements
  Potential use of the same ionic liquid catalyst for oligomerization and alkylation steps
  Improved branching characteristics of the product
  Increased overall molecular weight of the product
  Incorporation of low cost feed (isoparaffins) to increase liquid yield of high value distillate fuel or lubricant components
  Production of a base oil or lubricant component having unique, high value properties

EXAMPLES

Example 1

Preparation of Fresh 1-Butyl-pyridinium Chloroaluminate Ionic Liquid 1-butyl-pyridinium chloroaluminate is a room temperature ionic liquid prepared by mixing neat 1-butyl-pyridinium chloride (a solid) with neat solid aluminum trichloride in an inert atmosphere. The syntheses of 1-butyl-pyridinium chloride and the corresponding 1-butyl-pyridinium chloroaluminate are described below. In a 2-L Teflon-lined autoclave, 400 gm (5.05 mol.) anhydrous pyridine (99.9% pure purchased from Aldrich) were mixed with 650 gm (7 mol.) 1-chlorobutane (99.5% pure purchased from Aldrich). The neat mixture was sealed and let to stir at 125° C. under autogenic pressure over night. After cooling off the autoclave and venting it, the reaction mix was diluted and dissolved in chloroform and transferred to a three liter round bottom flask. Concentration of the reaction mixture at reduced pressure on a rotary evaporator (in a hot water bath) to remove excess chloride, unreacted pyridine and the chloroform solvent gave a tan solid product. Purification of the product was done by dissolving the obtained solids in hot acetone and precipitating the pure product through cooling and addition of diethyl ether. Filtering and drying under vacuum and heat on a rotary evaporator gave 750 gm (88% yields) of the desired product as an off-white shinny solid. $^1$H-NMR and $^{13}$C-NMR were ideal for the desired 1-butyl-pyridinium chloride and no presence of impurities was observed by NMR analysis.

1-Butyl-pyridinium chloroaluminate was prepared by slowly mixing dried 1-butyl-pyridinium chloride and anhydrous aluminum chloride ($AlCl_3$) according to the following procedure. The 1-butyl-pyridinium chloride (prepared as described above) was dried under vacuum at 80° C. for 48 hours to get rid of residual water (1-butyl-pyridinium chloride is hydroscopic and readily absorbs water from exposure to air). Five hundred grams (2.91 mol.) of the dried 1-butyl-pyridinium chloride were transferred to a 2-Liter beaker in a nitrogen atmosphere in a glove box. Then, 777.4 gm (5.83 mol.) of anhydrous powdered $AlCl_3$ (99.99% from Aldrich) were added in small portions (while stirring) to control the temperature of the highly exothermic reaction. Once all the AlCl₃ was added, the resulting amber-looking liquid was left to gently stir overnight in the glove box. The liquid was then filtered to remove any un-dissolved AlCl₃. The resulting acidic 1-butyl-pyridinium chloroaluminate was used as the catalyst for the Examples in the Present Application.

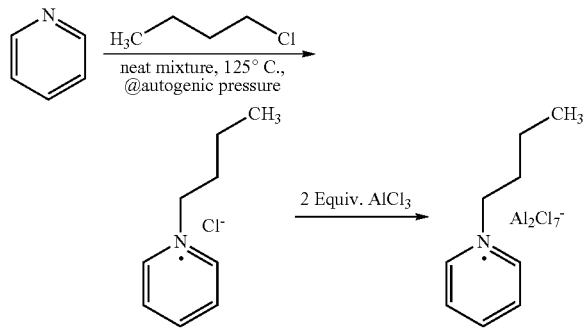

Example 2

Oligomerization of 1-Decene

One process for making high quality oils is by oligomerization of olefins followed by a separate step of alkylation with an isoparaffin. Olefin oligomers exhibit good physical lubricating properties. However, introducing short chain branching in the oligomers enhances the properties of the final products. Introducing the branching can be done by alkylation of the oligomers with isoparaffins. Alkylation of the oligomeric products is also a route to reducing the olefinicity of the oligomers and, hence, producing chemically and thermally more stable oligomers. The process is exemplified by alkylation of 1-decene oligomers (described below).

Oligomerization of 1-decene and alkylation of the oligomer were done according to the procedures described below. In a 300 cc autoclave equipped with an overhead stirrer, 100 gm of 1-decene was mixed in with 20 gm of 1-methyl-tributyl ammonium chloroaluminate. A small amount of HCl (0.35 gm) was introduced to the mix as a promoter and the reaction mix was heated to 50° C. with vigorous stirring for 1 hr. Then, the stirring was stopped and the reaction was cooled down to room temperature and let to settle. The organic layer (insoluble in the ionic liquid) was decanted off and washed with 0.1 N KOH. The organic layer was separated and dried over anhydrous MgSO₄. The colorless oily substance was analyzed by SIMDIST. The oligomeric product has a Bromine Number of 7.9. Table 1 below shows the SIMDIST analysis of the oligomerization products.

Example 3

Alkylations of 1-Decene Oligomers

The oligomers of 1-decene made as described in example 2 were alkylated with isobutane in 1-butylpyridinium chloroaluminate and in methyl-tributyl ammonium chloroaluminate (TBMA) ionic liquids according to the procedures described below. In a 300 cc autoclave fitted with an overhead stirrer, 26 gm of the oligomer and 102 gm of isobutane were added to 21 gm of methyl-tributyl-ammonium chloroaluminate ionic liquid. To this mixture, 0.3 gm of HCl gas was added and the reaction was heated to 50° C. for 1 hr while stirring at >1000 rpm. Then the reaction was stopped and the products were collected in a similar procedure as described above for the oligomerization reaction. The collected products, colorless oils, have a Bromine Number of 3.2. Table 1 shows the SIMDIST analysis of the oligomer alkylation products.

Alkylation of the oligomer was repeated using the same procedure described above, but 1-butylpyridinium chloroaluminate was used in place of methyl-tributyl-ammonium chloroaluminate. Alkylation of the oligomer in butylpyridinium gave a product with a bromine index of 2.7. The SIMDIST data is shown in Table 1.

TABLE 1

| SIMDIST TBP (WT %) | 1-Decene Oligomers ° F. | 1-Decene oligomers Alkylation in 1-butylpyridinium chloroaluminate | 1-Decene oligomers alkylation in TBMA |
|---|---|---|---|
| TBP@0.5 | 330 | 298 | 296 |
| TBP@5 | 608 | 341 | 350 |
| TBP@10 | 764 | 574 | 541 |
| TBP@15 | 789 | 644 | 630 |
| TBP@20 | 856 | 780 | 756 |
| TBP@30 | 944 | 876 | 854 |
| TBP@40 | 1018 | 970 | 960 |
| TBP@50 | 1053 | 1051 | 1050 |
| TBP@60 | 1140 | 1114 | 1118 |
| TBP@70 | 1192 | 1167 | 1173 |
| TBP@80 | 1250 | 1213 | 1220 |
| TBP@90 | 1311 | 1263 | 1268 |
| TBP@95 | 1340 | 1287 | 1291 |
| TBP@99.5 | 1371 | 1312 | 1315 |

Example 4

Oligomerization of 1-Decene in Ionic Liquids in the Presence of iso-Butane

Oligomerization of 1-decene was carried out in acidic 1-butyl-pyridinium chloroaluminate in the presence of 10 mole % of isobutane. The reaction was done in the presence of HCl as a promoter. The procedure below describes, in general, the process. To 42 gm of 1-butyl-pyridinium chloroaluminate in a 300 cc autoclave fitted to an overhead stirrer, 101 gm of 1-decene and 4.6 gm of isobutane were added and the autoclave was sealed. Then 0.4 gm of HCl was introduced and the stirring started. The reaction was heated to 50° C. The reaction was exothermic and the temperature quickly jumped to 88° C. The temperature in few minutes went back down to 44° C. and was brought up to 50° C. and the reaction was vigorously stirred at about 1200 rpm for an hour at the autogenic pressure (~atmospheric pressure in this case). Then, the stirring was stopped and the reaction was cooled to room temperature. The contents were allowed to settle and the organic layer (immiscible in the ionic liquid) was decanted off and washed with 0.1 N KOH aqueous solution. The colorless oil was analyzed with simulated distillation and bromine analysis. The Bromine Number was 2.6. The Bromine Number is much less than that usually observed for the 1-decene oligomerization in the absence of isobutane. The Bromine Number for 1-decene oligomerization in the absence of iC₄ is in the range of 7.5-7.9 based on the catalyst, contact time and catalyst amounts used in the oligomerization reaction. The Simulated Distillation data is shown in Table 3.

The Simulated Distillation data in Tables 1 and 3 show that alkylations of the already made 1-decene oligomers with isobutane and the simultaneous oligomerization/alkylation of 1-decene lead to fairly comparable products. The overall outcome of the two operations is amazingly close in the products boiling ranges and olefinic contents as indicated by bromine numbers shown in Table 2.

Table 2 compares the Bromine Numbers of the starting 1-decene, 1-decene oligomerization products in the presence of $iC_4$, 1-decene oligomerization products without $iC_4$, and the alkylation products of 1-decene oligomers with excess $iC_4$.

TABLE 2

| Material | 1-Decene | Oligomerization-alkylation of 1-Decene with 10 mol % $iC_4$ | Oligomerization Products of 1-Decene/No $iC_4$ | Alkylated 1-decene oligomers |
|---|---|---|---|---|
| Bromine Number | 114 | 2.6 | 7.9 | 2.8 |

The data above suggests that the chemistry can be done by either alkylating the oligomers in situ (where isoparaffins are introduced into the oligomerization reactor) or in consecutive steps to oligomerization of an alpha olefin. In both processes, the yielded products are close in their properties. In the simultaneous oligomerization-alkylation scheme, the desired alkylated oligomeric products can be made in one single step and, thus, can be an economically advantageous process. However, the two step process with two separate reaction zones where each can be optimized independently, provides greater chances for tailoring and tuning the conditions to make products with particularly desired properties.

Example 5

Oligomerization of 1-Decene in Ionic Liquids in the Presence of Varying iso-Butane Concentrations Oligomerization of 1-decene was carried out in acidic 1-butyl-pyridinium chloroaluminate in the presence of varying mole % of isobutane. The reaction was done in the presence of HCl as a promoter (co-catalyst). The procedure below describes, in general, the process. To 42 gm of 1-butyl-pyridinium chloroaluminate in a 300 cc autoclave fitted to an overhead stirrer, 101 gm of 1-decene and 4.6 gm of isobutane were added and the autoclave was sealed. Then 0.2-0.5 gm of HCl was introduced into the reactor, and then, started the stirring. The reaction is exothermic and the temperature quickly jumped to 88° C. The temperature dropped down quickly to the mid 40s and was brought up to 50° C. and kept at around 50° C. for the remainder of the reaction time. The reaction was vigorously stirred for about an hour at the autogenic pressure. The stirring was stopped, and the reaction was cooled to room temperature. The contents were allowed to settle and the organic layer (immiscible in the ionic liquid) was decanted off and washed with 0.1 N KOH aqueous solution. The recovered oils were characterized with simulated distillation, bromine analysis, viscosity, viscosity indices, and pour and cloud points.

Table 3, below, show the properties of the resulting oils of different 1-decene/isobutane ratios. All the reactions were run for approximately 1 hr at 50° C. in the presence of 20 gm of ionic liquid catalyst.

TABLE 3

| n | $C_{10}^-/iC4 = 0.8$ | $C_{10}^-/iC_4 = 1$ | $C_{10}^-/iC_4 = 4$ | $C_{10}^-/iC_4 = 5.5$ | $C_{10}^-/iC_4 = 9$ |
|---|---|---|---|---|---|
| TBP @0.5 | 301 | 311 | 322 | 329 | 331 |
| TBP @5 | 340 | 382 | 539 | 605 | 611 |
| TBP @10 | 440 | 453 | 663 | 746 | 775 |
| TBP @20 | 612 | 683 | 792 | 836 | 896 |
| TBP @30 | 798 | 842 | 894 | 928 | 986 |
| TBP @40 | 931 | 970 | 963 | 999 | 1054 |
| TBP @50 | 1031 | 1041 | 1007 | 1059 | 1105 |
| TBP @60 | 1098 | 1099 | 1067 | 1107 | 1148 |
| TBP @70 | 1155 | 1154 | 1120 | 1154 | 1187 |
| TBP @80 | 1206 | 1205 | 1176 | 1200 | 1228 |
| TBP @90 | 1258 | 1260 | 1242 | 1252 | 1278 |
| TBP @95 | 1284 | 1290 | 1281 | 1282 | 1305 |
| TBP @99.5 | 1311 | 1326 | 1324 | 1313 | 1335 |

The data shown in Table 3 indicates that the amount of isobutane added to the reaction does influence the boiling range of the produced oils. As shown in Table 3, there are more products in the lower boiling cuts when higher concentrations of isobutane are used in the reaction. This indicates that more alkylation is taking part directly with 1-decene and 1-decene dimers rather than with higher oligomers when higher isobutane concentrations are present in the reaction zone. When more isobutane is present more alkylation can occur, and 1-decene alkylation with $iC_4$ to make $C_{14}$ and 1-decene dimer alkylation to make $C_{24}$ will be more prevalent than at lower concentrations of isobutane. Therefore, the degree of branching and oligomerization can be tailored by the choice of olefins, isoparaffins, olefin/isoparaffin ratios, contact time and the reaction conditions.

The alkylated oligomers will no longer take part in further oligomerization due to "capping" off their olefinic sites, and the final oligomeric chain will be shorter perhaps than the normal oligomeric products, but with more branching. While the oligomerization pathway is the dominant mechanism, it is very clear that the alkylation of 1-decene and its oligomers with isobutane does take part in the chemistry.

Table 4, below, compares some physical properties of the products obtained from the reactions of Table 3

TABLE 4

|  | $C10^=/iC_4 = 0.8$ | $C10^=/iC_4 = 1$ | $C10^=/iC_4 = 4$ | $C10^=/iC_4 = 5.5$ | $C10^=/iC_4 = 9$ |
|---|---|---|---|---|---|
| VI | 145 | 171 | 148 | 190 | 150 |
| Vis@100 | 9.84 | 7.507 | 9.73 | 7.27 | 11.14 |
| VIS@40 | 61.27 | 37.7 | 59.63 | 33.5 | 70.21 |
| Pour Point | −42 | −42 |  | −44 | −52 |
| Cloud Point | −63 | −64 |  | −69 | −28 |
| Bromine Number | 3.1 | 0.79 | 2.2 | 3.8 | 6.1 |

The oligomerization/alkylation run @ 1-decene/iC$_4$ ratio of 5.5 was repeated several times at the same feed ratios and conditions. The viscosity@100° C. in the repeated samples ranged from 6.9-11.2 cSt. The VI ranged from 156-172. All the repeated samples contained low boiling cuts (below 775° F.) ranging from 10%-15%. The low boiling cut appears to influence the VI.

The Bromine Numbers shown in Table 4 are much less than usually observed for the 1-decene oligomerization in the absence of isobutane. The Bromine Number for 1-decene oligomerization in the absence of iC$_4$ is in the range of 7.5-7.9 based on the catalyst, contact time and catalyst amounts used in the oligomerization reaction. Table 5, below, compares the Bromine Number analysis of 1-decene, simultaneous oligomerization and alkylation of 1-decene, 1-decene oligomerization only products, and the alkylated oligomers (oligomerization followed by alkylation). By looking at these values, one can see the role of the incorporation of isobutane on the olefinicity of the final products.

TABLE 5

| Material | 1-Decene | Oligomerization with 10 mol % iC$_4$, (20 mol % iC$_4$) | 1-Decene Oligomerization | Alkylated 1-decene oligomers with iC$_4$ |
|---|---|---|---|---|
| Bromine Number | 114 | 6.1, (2.2) | 7.9 | 2.8 |

Example 6

Oligomerization of a Mixture of Alpha Olefins in the Presence of iso-Butane

A 1:1:1 mixture of 1-hexene:1-octene:1-decene was oligomerised in the presence of isobutane at the reaction conditions described earlier for oligomerization of 1-decene in the presence of isobutane (100 gm olefins, 20 gm IL catalyst, 0.25 gm HCl as co-catalyst, 50° C., autogenic pressure, 1 hr). The products were separated from the IL catalyst, and the IL layer was rinsed with hexane, which was decanted off and added to the products. The products and the hexane wash were treated with 0.1 N NaOH to remove any residual AlCl$_3$. The organic layers were collected and dried over anhydrous MgSO$_4$. Concentration (on a rotary evaporator at reduced pressure, in a water bath at ~70° C.) gave the oligomeric product as viscous yellow oils. Table 6 below shows the Simulated Distillation, viscosity, and pour point, cloud point, and bromine number data of the alkylated oligomeric products of the olefinic mixture in the presence of isobutane.

TABLE 6

| SIMDIST TBP (WT %), | Oligomers of C$_6^=$, C$_8^=$, C$_{10}^=$ W/iC$_4$ ° F. |
|---|---|
| TBP @0.5 | 313 |
| TBP @5 | 450 |
| TBP @10 | 599 |
| TBP @15 | 734 |
| TBP @20 | 831 |
| TBP @30 | 953 |
| TBP @40 | 1033 |
| TBP @50 | 1096 |
| TBP @60 | 1157 |
| TBP @70 | 1220 |
| TBP @80 | 1284 |
| TBP @90 | 1332 |
| TBP @95 | 1357 |
| TBP @99.5 | 1384 |
| Physical Properties: |  |
| VI | 140 |
| VIS@100° C. | 7.34 CST |
| VIS@40° C | 42 CST |
| Pour Point | −54° C. |
| Cloud Point | <−52° C. |
| Bromine # | 3.1 |

As shown in the data above, high quality oils with desirable lubricating properties can be made by either simultaneous olefin oligomerization/alkylation, or by oligomerization of the appropriate olefins followed by alkylation of the oligomeric products. Regardless of the process, the oils produced in both processes appear to be close in their boiling ranges, olefinicity and physical properties such as viscosity indices, viscosities, pour points and cloud points. Both process lead to oils with appreciable concentrations of branched paraffins formed by capping (alkylating) olefins and their oligomers and low olefin concentrations.

What is claimed is:

1. A lubricant component or base oil, possessing:
   a cloud point of less than −50° C.;
   a VI of at least 134;
   a difference between the T90 and T10 boiling points of at least 300° F. by SIMDIST; and
   a Bromine Number of less than 0.2.

2. The lubricant component or base oil of claim 1, wherein the cloud point is less than −52° C.

3. The lubricant component or base oil of claim 2, wherein the cloud point is less than −55° C.

4. The lubricant component or base oil of claim 1, wherein the VI is at least 140.

5. The lubricant component or base oil of claim 4, wherein the VI is at least 145.

6. The lubricant component or base oil of claim 1, wherein the VI is from at least 134 to 190.

7. The lubricant component or base oil of claim 6, wherein the VI is from at least 140 to 190.

8. The lubricant component or base oil of claim 7, wherein the VI is from at least 145 to 190.

9. The lubricant component or base oil of claim 8, wherein the VI is from 156 to 172.

10. The lubricant component or base oil of claim 1, additionally possessing a kinematic viscosity at 100° C. from 6.9 to 11.2 cSt.

11. The lubricant component or base oil of claim 1, made by a process comprising olefin oligomerization in an ionic liquid oligomerization zone.

12. A lubricant component or base oil, possessing:
a cloud point of less than −52° C.;
a VI of at least 140;
a difference between the T90 and T10 boiling points of at least 250° F. by SIMDIST; and
a Bromine Number of less than 0.2.

13. The lubricant component or base oil of claim 12, wherein the difference between the T90 and T10 boiling points is at least 300° F. by SIMDIST.

14. The lubricant component or base oil of claim 12, wherein the cloud point is less than −52° C.

15. The lubricant component or base oil of claim 14, wherein the cloud point is less than −55° C.

16. The lubricant component or base oil of claim 15, wherein the VI is at least 145.

17. The lubricant component or base oil of claim 12, wherein the VI is from at least 140 to 190.

18. The lubricant component or base oil of claim 17, wherein the VI is from at least 145 to 190.

19. The lubricant component or base oil of claim 12, additionally possessing a kinematic viscosity at 100° C. from 6.9 to 11.2 cSt.

20. The lubricant component or base oil of claim 12, made by a process comprising olefin oligomerization in an ionic liquid oligomerization zone.

* * * * *